United States Patent
Dlugach et al.

(10) Patent No.: US 10,238,339 B2
(45) Date of Patent: Mar. 26, 2019

(54) IMPLANTABLE DEVICE WITH BRIDGE

(71) Applicant: MICROTECH MEDICAL TECHNOLOGIES LTD., Tel Aviv (IL)

(72) Inventors: Yekaterina Dlugach, Mabuim (IL); Nadav Agian, Kfar Yona (IL)

(73) Assignee: Microtech Medical Technologies Ltd., Tel Aviv (IL)

( * ) Notice: Subject to any disclaimer, the term of this patent is extended or adjusted under 35 U.S.C. 154(b) by 536 days.

(21) Appl. No.: 14/211,397

(22) Filed: Mar. 14, 2014

(65) Prior Publication Data

US 2014/0276141 A1   Sep. 18, 2014

Related U.S. Application Data

(60) Provisional application No. 61/791,126, filed on Mar. 15, 2013.

(51) Int. Cl.
*A61B 5/02* (2006.01)
*A61B 5/00* (2006.01)
(Continued)

(52) U.S. Cl.
CPC ............ *A61B 5/686* (2013.01); *A61B 5/0215* (2013.01); *A61B 5/6876* (2013.01); *A61F 2/915* (2013.01);
(Continued)

(58) Field of Classification Search
CPC ... A61B 5/6882; A61B 5/6876; A61B 5/6862; A61B 5/686; A61B 5/145; A61B 5/026;
(Continued)

(56) References Cited

U.S. PATENT DOCUMENTS 5,591,197 A * 1/1997 Orth .................... A61F 2/07
                                                606/191
5,619,997 A   4/1997 Kaplan
(Continued)

FOREIGN PATENT DOCUMENTS

DE   197 46 882    4/1999
JP   2009-515582   4/2009
(Continued)

OTHER PUBLICATIONS

International Search Report and Written Opinion from corresponding PCT Application No. PCT/IB2014/001565 dated Dec. 2, 2014, 14 pages.

*Primary Examiner* — Christian Jang
*Assistant Examiner* — Karen Toth
(74) *Attorney, Agent, or Firm* — Cadwalader, Wickersham & Taft LLP

(57) ABSTRACT

This invention relates to an implantable device for a physiologic sensor, comprising an implantable expandable anchor, a bridge on which the sensor is secured, as well as an optional adapting ring. The invention also relates to a method of monitoring bodily functions using the anchor and sensor. The anchor is compressed and the bridge assumes an elongated shape during delivery to a target lumen. Upon deployment at the target site, the anchor expands and the bridge bows into the interior lumen of the expanded anchor, distancing the sensor from the vessel wall. This invention also relates to a method of manufacturing said device and a method of implanting a sensor.

26 Claims, 9 Drawing Sheets

(51) Int. Cl.
*A61B 5/0215* (2006.01)
*A61F 2/82* (2013.01)
*A61F 2/915* (2013.01)
*A61B 5/145* (2006.01)
*A61F 2/24* (2006.01)
*A61F 2/86* (2013.01)
*A61B 90/00* (2016.01)

(52) U.S. Cl.
CPC .............. *A61B 5/145* (2013.01); *A61B 5/6862* (2013.01); *A61B 2090/3966* (2016.02); *A61F 2/243* (2013.01); *A61F 2/86* (2013.01); *A61F 2002/825* (2013.01); *A61F 2002/91541* (2013.01); *A61F 2002/91575* (2013.01); *A61F 2002/91583* (2013.01); *A61F 2250/0039* (2013.01); *A61F 2250/0096* (2013.01); *Y10T 29/49826* (2015.01); *Y10T 29/49908* (2015.01)

(58) Field of Classification Search
CPC .......... A61B 2017/00867; A61B 5/021; A61B 5/14503; A61B 5/6839; A61F 2/915; A61F 2/01; A61F 2002/91575; A61F 2002/9155
See application file for complete search history.

(56) References Cited

U.S. PATENT DOCUMENTS

| | | | |
|---|---|---|---|
| 5,629,008 A | 5/1997 | Lee | |
| 5,755,781 A * | 5/1998 | Jayaraman | A61F 2/91 623/1.16 |
| 5,786,439 A * | 7/1998 | Van Antwerp | A61B 5/14865 427/2.12 |
| 5,984,947 A * | 11/1999 | Smith | A61B 17/12109 606/200 |
| 5,989,190 A | 11/1999 | Kaplan | |
| 5,992,000 A | 11/1999 | Humphrey et al. | |
| 6,063,102 A | 5/2000 | Morales | |
| 6,074,381 A | 6/2000 | Dinh et al. | |
| 6,082,990 A | 7/2000 | Jackson et al. | |
| 6,083,165 A | 7/2000 | Kaplan | |
| 6,092,273 A | 7/2000 | Villareal | |
| 6,108,886 A | 8/2000 | Kimes et al. | |
| 6,331,163 B1 | 12/2001 | Kaplan | |
| 6,387,118 B1 | 5/2002 | Hanson | |
| 6,660,021 B1 * | 12/2003 | Palmer | A61B 17/221 606/200 |
| 6,770,032 B2 | 8/2004 | Kaplan | |
| 7,134,341 B2 | 11/2006 | Girmonsky et al. | |
| 7,225,518 B2 | 6/2007 | Eidenschink et al. | |
| 7,415,883 B2 | 8/2008 | Kaplan | |
| 8,162,839 B2 | 4/2012 | Kaplan | |
| 9,119,656 B2 * | 9/2015 | Bose | A61B 17/22 |
| 9,452,039 B2 * | 9/2016 | Snow | A61F 2/01 |
| 2003/0009093 A1 | 1/2003 | Silver | |
| 2005/0055046 A1 * | 3/2005 | McGuckin, Jr. | A61F 2/01 606/200 |
| 2005/0075721 A1 | 4/2005 | Klein | |
| 2006/0004436 A1 | 1/2006 | Amarant et al. | |
| 2006/0122522 A1 * | 6/2006 | Chavan | A61B 5/0215 600/505 |
| 2007/0129637 A1 * | 6/2007 | Wolinsky | A61B 5/02152 600/486 |
| 2007/0191904 A1 | 8/2007 | Libbus et al. | |
| 2010/0274350 A1 | 10/2010 | Richter | |
| 2010/0324658 A1 | 12/2010 | Bogert | |
| 2012/0108922 A1 | 5/2012 | Schell et al. | |
| 2012/0271134 A1 * | 10/2012 | Allan | A61B 5/0215 600/373 |
| 2013/0060139 A1 | 3/2013 | Richter et al. | |

FOREIGN PATENT DOCUMENTS

| | | |
|---|---|---|
| JP | 2009-542421 | 12/2009 |
| RU | 2108765 C1 | 4/1998 |
| WO | WO 96/39102 | 12/1996 |
| WO | WO 01/97687 | 12/2001 |
| WO | WO 2011/056797 | 5/2011 |

* cited by examiner

IMPLANTABLE DEVICE WITH BRIDGE

FIELD OF THE INVENTION

This invention relates to a novel implantable device for a bodily sensor and a method of manufacturing said device.

BACKGROUND OF THE INVENTION

Implantable sensors provide real time readings for one or more physiological parameters in a patient. Sensors may be used for monitoring a variety of bodily properties, such as temperature, pressure, fluid flow, or biochemical properties. Implantable sensors, suitable for use within the body, are capable of remote data transmission and, in recent years, have become compact in size and long lasting.

Implantable sensors may be secured within a lumen or other bodily cavity using a variety of devices, for example, an anchor. Where an expandable anchor is used, the anchor is compressed for delivery through the blood vessels and expanded at a target site to engage the vessel wall. The sensor must be secured to the anchor while the compressed anchor is delivered, and remain secured once the anchor is expanded at the target site. Further, the sensor must maintain its ability to measure and transmit data following delivery and expansion. Thus, accurate placement of the anchor and sensor is critical for the reliable measurement of a selected physiological parameter. Inaccurate positioning of a sensor jeopardizes the integrity of the sensor's readings. For example, if the sensor is not in sufficient contact with the blood due to cellular ingrowth around the sensor, accurate blood pressure readings cannot be obtained.

In order to minimize endothelial cell growth around the sensor, it is desirable to position the sensor a distance from the vessel wall when the anchor is implanted. Positioning the sensor away from the vessel wall also reduces interference from the vessel tissue and reduces any cellular or plaque buildup on the sensor. However, because the anchor is generally pressed against the vessel wall to maintain its position in the vessel and the sensor is attached to the anchor, current anchoring systems do not generally permit a sensor to be displaced from the anchor. Therefore, there is a need for an anchor sensor device with a sensor capable of being compressed to maintain deliverability, yet maximize the accuracy of the sensor at the target site once the anchor is implanted.

SUMMARY OF THE INVENTION

The present invention relates to an implantable device for a sensor and a manufacturing process to produce said device. The implantable device comprises an expandable anchor and a bridge and a small passive sensor which is secured onto the bridge. The device facilitates positioning of the sensor in a lumen or a human blood vessel, so that the sensor may accurately obtain internal measurements of the environment, such as, e.g., fluid pressure, environmental temperature or chemical measurements. In addition, the device may be a device that is able to treat a medical condition, for example, by releasing a therapeutic agent.

The anchor comprises any structure or configuration that is compressible during delivery, decreasing its diameter, and expandable at the target site, increasing its diameter. A bridge is attached to the anchor. When said anchor is compressed during delivery, the bridge is generally aligned with the wall of the anchor. At the target site, the anchor is expanded, thereby increasing its diameter and the bridge adopts a bowed position, i.e., protruding into the lumen, distancing the center portion of the bowed bridge away from the vessel wall. Positioning the sensor on the bowed portion of the bridge improves the accuracy of the sensor's reading because it eliminates interference from the vessel wall and brings the sensor into direct contact with the measurand. The anchor may comprise any device, which changes in diameter from a compressed to an expanded configuration.

The bridge is an elongated member, aligned with the anchor's longitudinal axis and configured to bow toward the interior portion of the lumen upon expansion of the anchor. In one embodiment, the bridge is substantially straight along the longitudinal axis of the anchor. In another embodiment, the bridge includes one or more loops or curved portions. In all respects, the bridge is designed to bow into the central portion of the lumen upon expansion.

The bridge is adapted to house the sensor. As such, the sensor may be secured on the bridge by an adapting ring. Alternatively, the sensor may be embedded into the bridge. The bridge may further optionally comprise an angiographic marker to indicate the location and orientation of the sensor so that the sensor can be positioned precisely. After delivery to the implantation site and proper implanted, the bridge bows within the interior of the lumen, causing the secured sensor to be displaced from the walls of the implantation site. Sensor measurements may be taken frequently over the duration of the implant without further invasive procedures.

Another aspect of the invention relates to the manufacturing process for the implantable device described above. One method relates to making an implantable device comprising an expandable anchor, a bridge and a sensor, whereby the expandable anchor has a compressed and expanded configuration, said anchor having a longitudinal axis and forming an anchor wall, said bridge is aligned with the longitudinal axis of the anchor and aligned with the anchor wall when said anchor is in the compressed configuration, and said bridge protrudes into said lumen when said anchor is in the expanded configuration, comprising the steps of: (a) manufacturing of the bridge and anchor as a single unit, (b) heat treating the bridge and anchor to a thermomechanically preset shape, and (c) assembling of the adapting ring and sensor onto the bridge. The single unit bridge-anchor may for example be manufactured from a tube or laser cut into a flat metal sheet or planar metal sheet then rolled and welded into a tube as known in the art. The heat treating step may be carried out on a mandrel having a preselected divot formed into the shape the bowed bridge will assume after expansion. The assembling step may further trap the sensor between the adapting ring and the bridge. The method may further comprise crimping and securing the device on a delivery catheter. Optionally, an angiographic marker can be attached to the sensor.

Alternatively, the device may be manufactured from separate anchor and bridge components. This method relates to making an implantable device comprising an expandable anchor, a bridge and a sensor, whereby the expandable anchor has a compressed and expanded configuration, said anchor having a longitudinal axis and forming an anchor wall, said bridge is aligned with the longitudinal axis of the anchor and aligned with the anchor wall when said anchor is in the compressed configuration, and said bridge protrudes into said lumen when said anchor is in the expanded configuration, comprising the steps of: (a) manufacturing the anchor; (b) manufacturing the bridge; (c) heat treating the bridge to a thermomechanically preset shape (d) attaching the bridge to the anchor component; and (e) assembling the sensor to the bridge. The bridge may be attached to the anchor component by welding, adhesives or other known method for attaching such components. The method may further comprise crimping and securing the device on a delivery catheter. Optionally, an angiographic marker can be attached to the sensor. Step (d) may be performed prior to step (c). Also, step (e) may be performed prior to step (d).

Yet another aspect of this invention is to provide a method of implanting a sensor comprising: (a) preparing a device comprising an expandable anchor, a bridge and a sensor, whereby said expandable anchor has a compressed and expanded configuration, said anchor having a longitudinal axis and forming an anchor wall, said bridge is aligned with the longitudinal axis of the anchor and aligned with the anchor wall when said anchor is in the compressed configuration, and said bridge protrudes into said lumen when said anchor is in the expanded configuration; (b) delivering the device to a lumen; and (c) expanding the anchor, causing the bridge to protrude into said lumen; and (d) causing said sensor to protrude into said lumen.

DETAILED DESCRIPTION OF THE INVENTION

Figure 1:
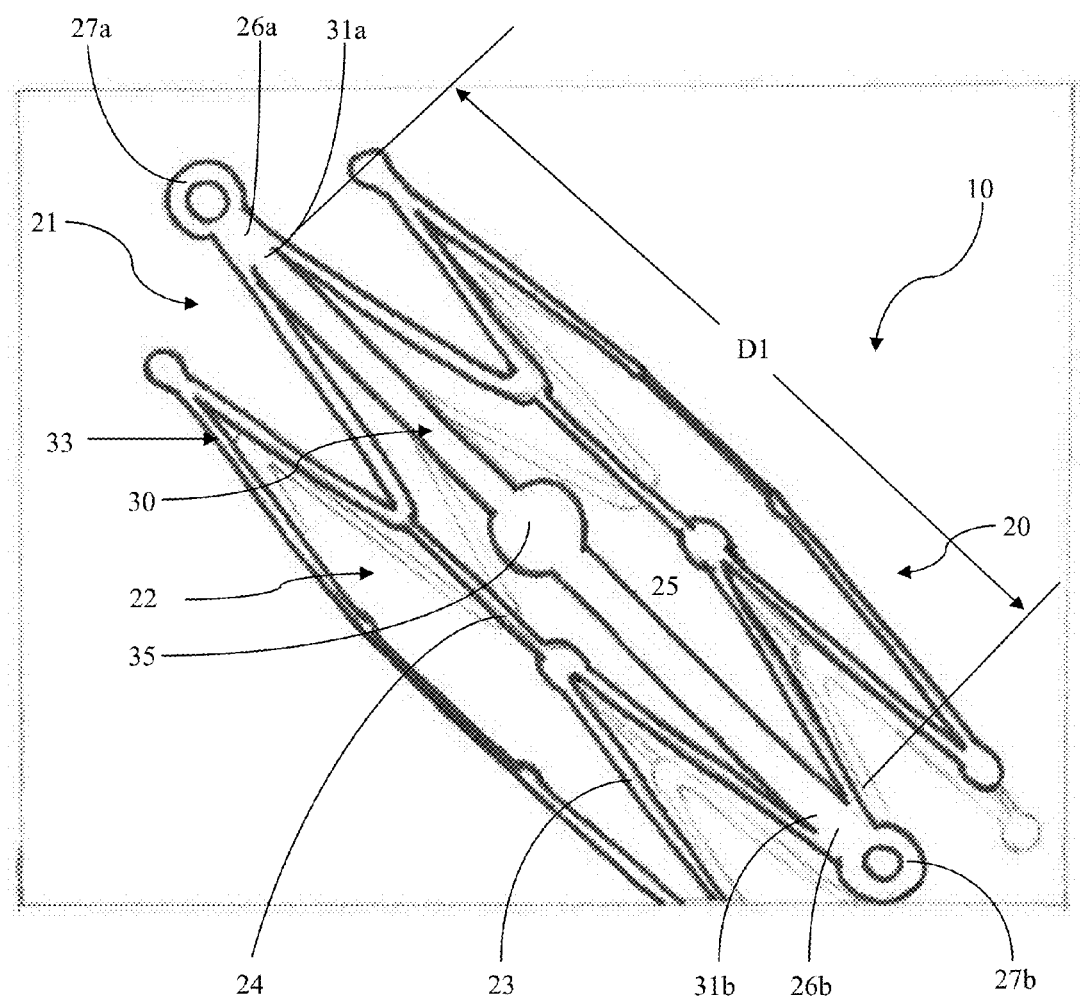
FIG. 1 illustrates one embodiment of the anchor device, including the anchor and the bridge, in the compressed configuration.

The present invention relates to an implantable device for a sensor and the manufacturing process to produce said device. The implantable device comprises an expandable anchor, a fixed and longitudinally-aligned bridge attached to the anchor and a sensor secured to the bridge.

Generally, the anchor may be a stent or any expandable prosthetic device, as is known in the art, preferably one having a plurality of undulating rings that are able to move relative to one another and foreshorten during the expansion of the anchor. The design of the undulating rings may vary as is known in the art. The undulating rings may comprise serpentine bands, loops or enclosed spaces as known in the art. In the compressed configuration of the anchor, the undulating rings are spaced apart from one another. When the anchor is deployed, at least a portion of a pair of neighboring undulating rings are configured to approach one another, decreasing the distance between said undulating rings. Other neighboring undulating rings do not necessarily move toward each other upon the anchor's expansion.

The bridge is preferably attached to a pair of neighboring undulating rings of the anchor. The bridge has a constant, fixed length that spans the distance between the adjacent connected undulating rings in the compressed position. In the compressed state of the anchor, the bridge maintains a position that is substantially aligned with the materials of the compressed anchor. Upon expansion of the anchor, the distance between the adjacent undulating rings decreases, and the bridge is configured to change position from its aligned position to the bowed position. The bowed position of the bridge effectively projects the bridge away from the wall of the anchor toward the center of the lumen. A sensor may be positioned at the apex of the bow of the bridge, or other areas away from the wall of the anchor, thereby protecting the sensor from the cellular growth of the vasculature and facilitating accurate readings at the implantation site. In either the compressed or expanded states of the anchor, the bridge maintains a constant, fixed length. One, two or a plurality of bridges may be attached to a single anchor.

In one embodiment, the bridge may possess comparable potential energy in the flat position and the bowed position, allowing it to transition back and forth between the two positions at the operator's discretion. This feature is advantageous when the anchor is capable of recompression and re-expansion after the initial deployment to achieve precise implantation. In another embodiment, the bridge may possess higher potential energy in the flat position than in the bowed position, similar to a flat spring. Upon deployment at the implantation site, the bridge bows to release the potential energy and facilitate the expansion of the anchor and thereafter may assist in locking the anchor in the expanded configuration.

The bridge may be manufactured as part of the anchor device as a single unit and is, in this way, attached to the anchor or may be manufactured separately and affixed to the anchor by welding or other methods known in the art. In another embodiment, a portion of the bridge can be manufactured as part of the anchor as a single unit while a separate portion of the bridge can be manufactured separately and affixed to the anchor or to a bridge portion unitary with the anchor, respectively. Laser or chemical etching from a material tube or sheet, or other manufacturing methods known in the art, may be adopted to manufacture the anchor and the bridge, separately or as a unitary structure. The bridge may be pretreated to the bowed position. Particularly when higher potential energy in the flat position is desired.

Generally, the sensor may be any implantable sensor known in the art. Preferably, the sensor is passive and miniature, allowing for real time readings of temperature, pressure, fluid flow, or other biochemical properties at the implantation site. Non-limiting examples of such a sensor are described in U.S. Pat. Nos. 5,619,997, 5,989,190, 6,083,165, 6,331,163, 6,770,032, 7,134,341, 7,415,883 and 8,162,839 (describing a protected or encapsulated sensor) and US Pub. No. 20130060139, the contents of which are herein incorporated by reference. The sensor may comprise a vibrating member capable of sensing the pressure of ambient fluid, and reading of the fluid pressure, which is transmittable wirelessly to a receiver outside the patient's body. The sensor and anchor may be implanted in any body lumen in which the recipient would benefit therefrom. Example lumens include arteries such as, e.g., the coronary arteries, carotid arteries and femoral arteries, as well as veins, such as, e.g., the portal or hepatic veins. For example, when implanted in the portal vein, such sensor allows the physician to monitor the portal vein blood pressure as often as is desired.

The sensor may be secured to the bridge by an adapting ring. The sensor is placed on the plate, an area of the bridge adapted to receive the sensor. The adapting ring surrounds the sensor and is affixed to the plate by means of adhesives or welding, thereby securing the sensor onto the bridge. Depending on the size and shape of the sensor, the adapting ring is shaped to secure the sensor on the surface of the bridge and allow exposure of the vibrating member of the sensor. Further, where the sensor has undesirable sharp corners, the adapting ring may cover the sharp corners of the sensor with its rounded shape. As such, the adapting ring may comprise any shape, preferably shapes devoid of sharp corners.

The anchor may be manufactured from biocompatible metal alloys (e.g., Nitinol) or polyesters (e.g., PET). The anchor is preferably self-expanding and made of a self-expanding material, such as Nitinol. For example, the anchor may comprise a metal alloy, such as a stainless steel, titanium, nickel-titanium (e.g., Nitinol), tantalum, cobalt-chromium, cobalt-chromium-vanadium, cobalt-chromium-tungsten, gold, silver, platinum, platinum-iridium, or any combination of the above metals and alloys. Alternatively, the anchor may comprise a biostable, non-bioabsorbable polymers, such as, for example, a polyethylene terephthalate (PET), polyurethane urea and silicone. In another alternative, the anchor may comprise an amorphous metal alloy, such as, for example, an alloy of iron, chromium, boron and phosphorus, as described in U.S. Pub. No. 2010/0274350, the contents of which are incorporated herein by reference. Preferably, anchor is capable of re-collapsing into a compressed configuration after it has been fully expanded. In this manner, the anchor may be retracted back within the delivery device if the initial deployment is not satisfactory, and then redeployed at another location. As a further alternative, the device may comprise a vehicle for local, controlled or sustained delivery of therapeutic agents, such as the device described in U.S. Pat. No. 5,629,008, the content of which are herein incorporated by reference.

The bridge may be made of the same material as the anchor and/or a different biocompatible non-thrombogenic, non-biodegradable and/or non-biofouling material. The adapting ring may be made of the same material as the anchor and/or the bridge, or a different biocompatible material that is non-thrombogenic, non-biodegradable and/or non-biofouling.

The present invention and its variant embodiments are explained below with reference to the accompanying drawings. The drawings are provided to facilitate an exemplary understanding of the present invention and to schematically illustrate particular embodiments of the invention. The skilled artisan will readily recognize other similar examples equally within the scope of the invention. The drawings are not intended to limit the scope of the present invention as defined in the appended claims.

FIG. 1 illustrates one embodiment of the invention, i.e., an implantable device 10 in the compressed configuration having anchor 20 in the radially compressed form and bridge 30 longitudinally aligned with said anchor. In the embodiment of FIG. 1, anchor 20 comprises a tubular shape with a longitudinal axis and a lumen 21 therethrough. Anchor 20 is composed of a plurality of serpentine members 23 longitudinally spaced along the length of the anchor. Each serpentine member 23 is composed of a plurality of peaks and valleys, wherein each peak points toward the distal end of the anchor and each valley points toward the proximal end of the anchor. Each serpentine member 23 is connected to a longitudinally adjacent serpentine member by connectors 24. Connectors, although shown in FIG. 1, are not required features of the inventive anchor, but rather are particular to the embodiment of FIG. 1. In FIG. 1, connector 24 extends from the peak of a first serpentine member to the valley of a second serpentine member. The length of connector 24 may be varied as needed in order to adjust the length of D1, and is not limited to the length shown in FIG. 1. Connectors 24 may further comprise one or more pinch points 28, shown in FIG. 2, which assist the anchor in recollapsing to the compressed configuration after expansion, if desired. The design of the peaks and valleys of the stent may vary as is known in the art, provided that the distance between the points of connection of the bridge to the stent decreases upon expansion of the stent.

An enclosed space, cell 25, is formed by the arrangement of serpentine members and connectors. A plurality of cells 25 aligned circumferentially around the stent defines wall 22, the external envelope of the anchor 20. In the compressed configuration as in FIG. 1, anchor 20 has a smaller diameter than in the expanded configuration. The length and diameter of anchor 20 in the compressed configuration may be sized as necessary for expansions in the target vessel, as is known in the analogous stent art. Anchor 20 may be any anchor or stent commonly used in percutaneous cardiovascular procedures or otherwise, including bare-metal stents and drug eluting stents.

As shown in FIG. 1, bridge 30 is attached to anchor 20. The bridge 30 comprises ends 31a and 31b, as well as plate 35 located between ends 31a and 31b. The length of the bridge spans distance, D1, in the compressed configuration. In FIG. 1, bridge 30 connects a first serpentine ring 23 at end 31b to a second serpentine ring 23 at end 31a. End 31b is connected to a first serpentine ring while end 31a is connected to a second serpentine ring.

In FIG. 1, cell 25 has points 26a and 26b located at the opposite vertices along the longitudinal axis. The two ends 31a and 31b are attached to points 26a and 26b, respectively. Cells of anchor 20 may be heterogeneous in size and shape. Bridge 30 may be attached to any cell of anchor 20. Further, bridge 30 may be made of the same material as anchor 20, or it may be made of a different biocompatible material.

In FIG. 1, points 26a and 26b may each further include ring 27a and 27b, respectively. Rings 27a and 27b are structural aspects of the anchor 20 that aid in the attachment of bridge 30 to the anchor 20, providing a point of attachment for the bridge to be affixed onto the anchor where the bridge is manufactured separately from the anchor. Further, rings 27a and 27b may function to relieve the strain on the anchor as the anchor expands in diameter and the bridge 30 becomes bowed. While rings 27a and 27b are illustrated as having a circular shape in FIG. 1, they are not limited to this shape. Non-circular shapes for rings 27a and b may be used to attach bridge 30 to anchor 20. Further, rings 27a and 27b need not be the same shape or size. For example, ring 27a may be larger than ring 27b, or vice versa. The attachment of the bridge 30 to anchor 20 may be achieved by any method known in the art, such as welding, soldering, or brazing, as will be further discussed herein.

Figure 2:
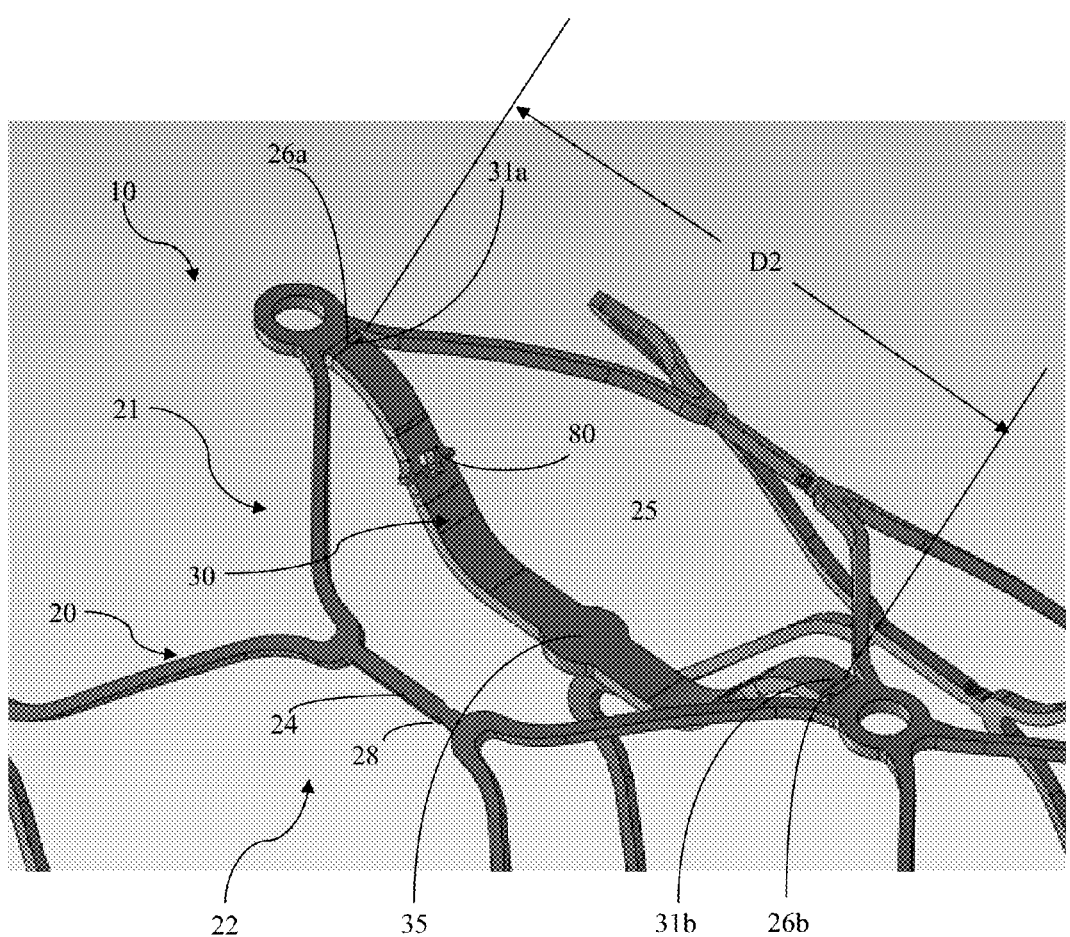
FIG. 2 illustrates the device in FIG. 1 in the expanded configuration.
Figure 6:
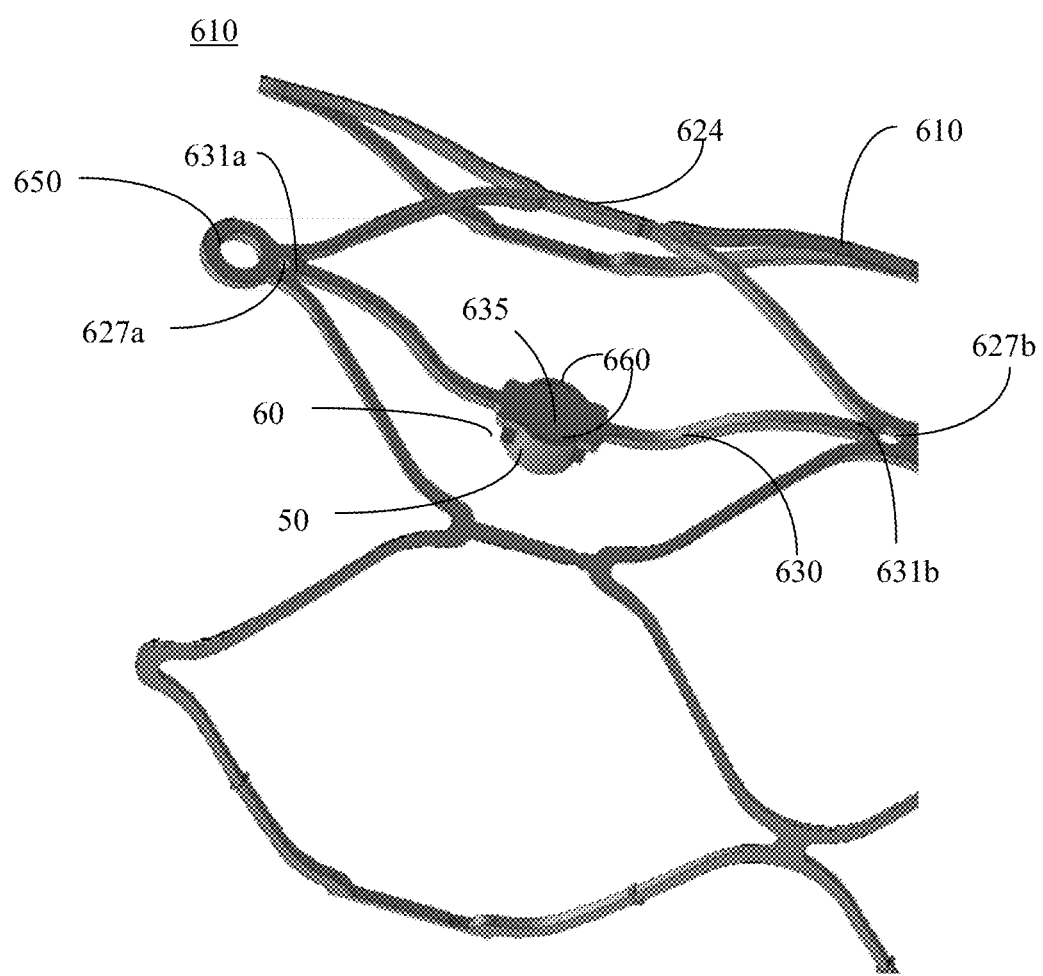
FIG. 6 illustrates an alternative embodiment of the bridge and anchor in the expanded configuration.

FIG. 1 illustrates the anchor 20 in the compressed configuration. In this state, D1 is the distance between points 26a and 26b, and bridge 30 spans D1. Further, bridge 30 does not protrude into the lumen of anchor 20 and as such is aligned with the members of the anchor when compressed. The length of the bridge may be any length as desired so long as the bridge bows within the lumen as the anchor expands. In the embodiment shown in FIG. 1, the bridge 30 has the same length as D1. In another embodiment, e.g., FIG. 3, the bridge 30 contains loops and may be longer than D1. The width and thickness of the bridge may be any size as desired. For example, the width and thickness may be greater than that of the anchor, as shown in FIGS. 1 and 2. Alternatively, the width and thickness of the bridge may be substantially equal to those of the members of the anchor, as shown in FIG. 6.

In FIG. 1, plate 35 is located at or near the middle point of bridge 30, and may have a larger width than the adjacent portions of the bridge. Plate 35 may be located at any location along bridge 30, and not necessarily at the center location depicted in FIG. 1. Plate 35 is configured to allow attachment of the sensor and the optional adapting ring thereto. The plate 35 is sized such that plate 35 covers the entire area of the sensor. Further, the size of the plate may be varied independently from the width and thickness of the remaining portions of the bridge. For example, in FIGS. 1 and 2, the plate 35 has a rounder shape as compared to the irregular shape of the plate 45 in FIG. 3, because the width of the bridge is greater in FIGS. 1 and 2 as compared to bridge 40 of FIG. 3. The plate 35 may have any shape in order to house the sensor. In an alternative embodiment, not shown, the plate may contain an orifice such that the sensor can be placed within the orifice of the sensor, and further secured by an adapting ring.

FIG. 2 illustrates the implanted device 10 of FIG. 1 in the expanded configuration. Anchor 20 is radially expanded and the diameter of lumen 21 is enlarged compared to that of the compressed anchor 20 of FIG. 1. In this configuration, cell 25 shortens in the longitudinal direction and widens in the circumferential direction compared to cell 25 in the compressed configuration. The overall length of the anchor 20 need not foreshorten so long as the distance between the adjacent undulating rings shortens, i.e., the foreshortening may be localized to the cell in which the bridge is located.

D2 in FIG. 2 is the distance between points 26*a* and 26*b* in the expanded configuration. The expansion of anchor 20 causes points 26*a* and 26*b* to move towards each other along the longitudinal axis, and D2 of FIG. 2 is smaller than D1 of FIG. 1. During delivery, the implantable device is radially constrained within a delivery catheter and the bridge 30 is aligned with wall 22. Expansion of the anchor results in a decrease in distance between points 26*a* and 26*b*, pushing ends 31*a* and 31*b* towards each other. When anchor 20 is expanded, bridge 30 is configured to maintain a constant length, which is the same distance between ends 31*a* and 31*b* in the compressed configuration of the anchor. As a result, the bridge adopts the bowed position shown in FIG. 2, protruding into the lumen of anchor 20. As the bridge bows, plate 35 also protrudes into lumen 21. The bowed position of bridge 30 keeps plate 35 and any sensor located thereupon distanced from the vessel wall (sensor not depicted in FIG. 2). The bridge can be configured to protrude into the lumen 21 so that plate 35 is any distance away from wall 22. In one embodiment, the bridge is configured so that plate 35 is in the center of the target vessel. In another embodiment, the bridge may be configured so that the apex of the bow is at least 2.5 mm away from wall 22. In FIG. 2, bridge 30 further comprises weld point 80, the area where the bridge can be welded to the anchor. Weld points are not limited to the location shown in FIG. 2, and may be located at any location on the bridge.

The bridge may be pretreated so that it assumes the desired bow shape in the expanded anchor. For example, when the bridge is made of metal, it may be pretreated to assume a bowed shape before assembled into the device. Non-limiting examples of methods of pretreatment may include stamping and heat treatment.

Although the devices illustrated in the figures comprise one bridge, the implantable device may include a plurality of bridges on one or more cells with the same or different sensors secured on each bridge to measure multiple physiological parameters (not illustrated). When the device contains more than one bridge, the bridges may be positioned on the anchor such that they may bow independently of one another.

Figure 3:
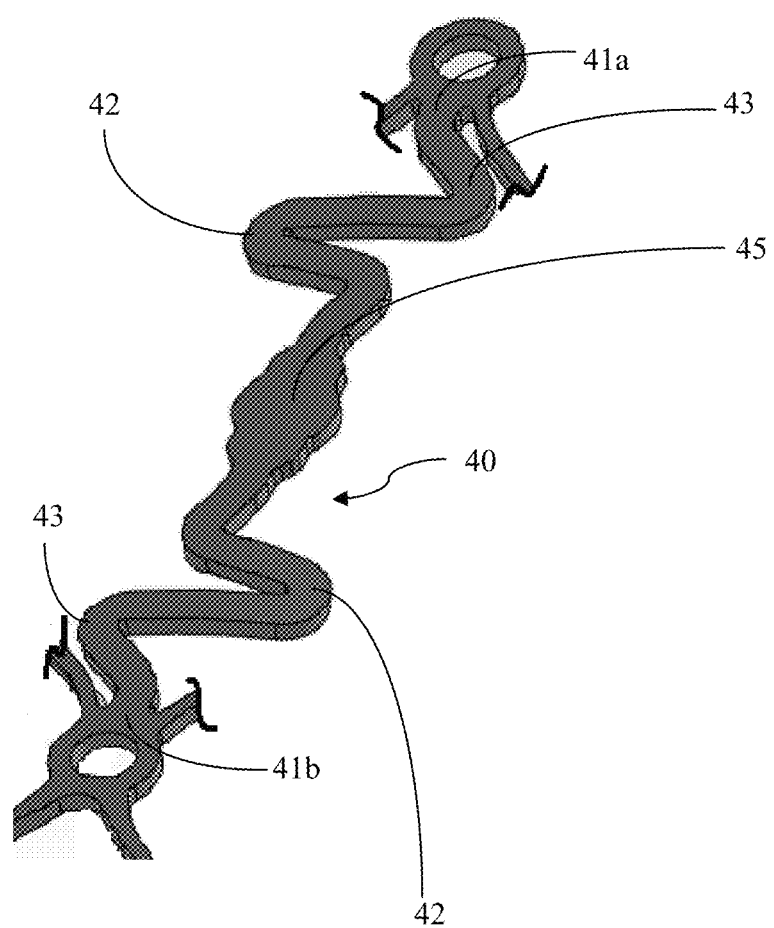
FIG. 3 illustrates a loop-containing-bridge embodiment of the device

FIG. 3 illustrates another embodiment of the bridge 40. Bridge 40 comprises a plate 45, used as an attachment site for the sensor, and an arrangement of loops 42, 43. Ends 41*a* and 41*b* are located at opposite ends of the bridge 40. Bridge 40 comprises a pair of loops 42 and 43 on each side of plate 45. In an alternate embodiment (not shown), more or fewer loops may be incorporated on either side of plate 45 of the bridge, and the plate 45 may be located at any position on the bridge. The loops may have any amplitude desired, and the loops need not have identical amplitude within a single bridge. In FIG. 3, bridge 40 is flattened and all portions are in the same plane, and loops 42 and 43 are positioned substantially perpendicular from bridge ends 41*a* and 41*b*, respectively. The loops on each side of plate 45 are symmetrical with respect to the middle point of bridge 40. In this embodiment, the loops facilitate the formation of a bowed position as the anchor expands. Further, the number and type of loops may be used to adjust the distance of the bridge away from the luminal wall. The flexibility of the bridge may be incurred with more loops, and decreased with fewer loops.

When the anchor is expanded, points 41*a* and 41*b* are pushed toward each other, shortening the longitudinal extension of cell 25, and bridge 40 bows, flexing at loops (42 and 43). Similar to the straight-bridge embodiment of FIGS. 1-2, plate 45 protrudes into lumen 21 when bridge 40 is in the bowed position, maintaining plate 45 a pre-selected distance from wall 22. When bridge 40 is bowed, the loops are configured to substantially straighten so that the plate 45 protrudes into the lumen.

Figure 5:
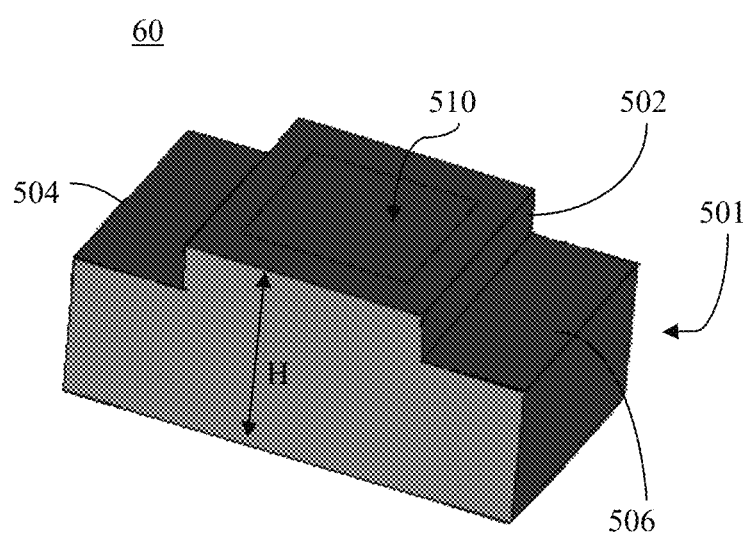
FIG. 5 illustrates one embodiment of a sensor used in this invention.

FIG. 5 illustrates sensor 60 aside from the bridge and adapting ring. Sensor 60 comprises housing 501 and vibrating member 510. The vibrating member 510 may be configured to collect data related to temperature, pressure, fluid flow, or other biochemical properties, as known in the art. The sensor 60 is configured to be interrogable and communicable with devices outside the body, e.g., a transducer. Sensor housing 501 may contain other components of the sensor, as is also well-known and described in the art cited above. As shown in FIG. 5, vibrating member 510 is located on a raised housing section 502 of housing 501.

Lower housing section 504 and 506 are located on each side of raised housing section 502. The dimensions of sensor 60 are not limited to the scale shown in FIG. 5. The height (H) of the sensor 60, as well as that of raised housing section 502 may be modified as needed by methods known in the art. Further, the width and length of the housing 501, as well as that of lower housing sections 504 and 506 may be modified as needed by methods known in the art. The sensor, as described above, is suitable for placement on the bridge as the vibrating member 510 is exposed to the external environment, and the dimensions of the sensor are adaptable for securement by the adapting ring, as further described below. The entire sensor as shown in FIG. 5 is small, e.g., between 0.005 to 0.3 mm$^3$ in volume.

While the sensor 60 of FIG. 5 comprises a rectangular shape, sensors used in this invention may comprise any suitable shape, as described, for example, in U.S. Pat. No. 8,162,839, the contents of which are incorporated herein by reference. Sensor 60 may be configured to take a variety of data measurements, such as physical or chemical measurements, including, for example, blood pressure, temperature, fluid flow, or sugar, mineral, gas content or pressure or other chemical content. Further the sensor may be coated with a biocompatible polymer or gel, for example, PEG, as described, for example, in U.S. Pat. No. 5,786,439. In addition, the entire implantable device, i.e., anchor, bridge, adapting ring, may also be similarly coated.

Figure 4:
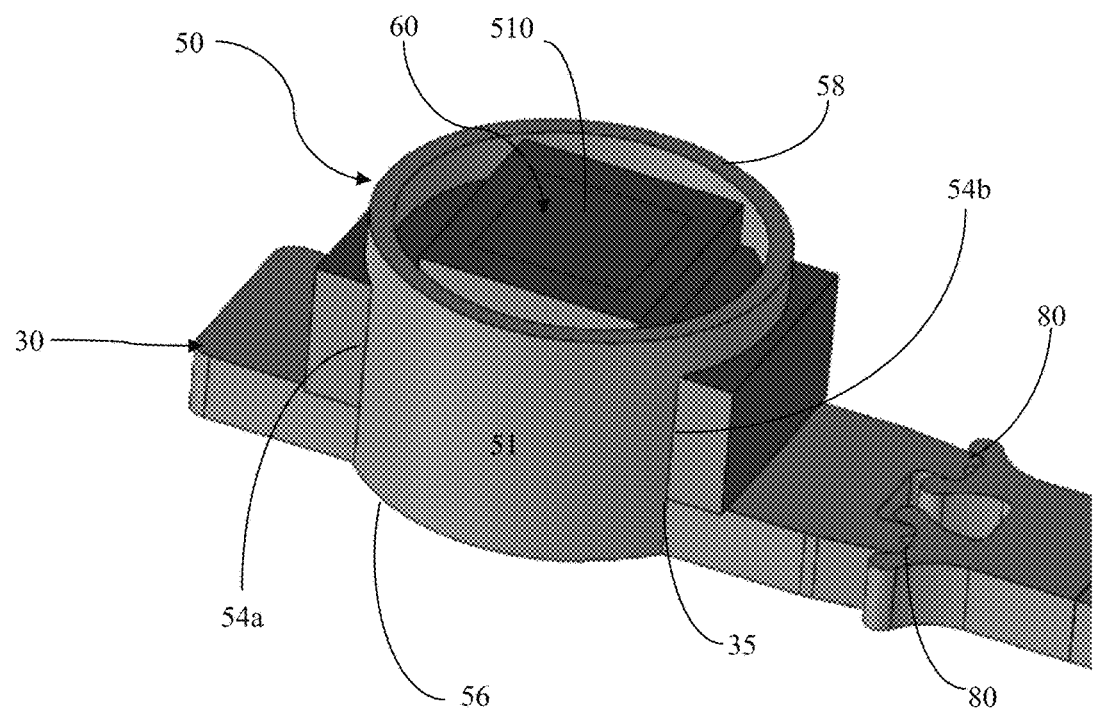
FIG. 4 illustrates a sensor secured to the bridge by an adapting ring.

FIG. 4 illustrates one embodiment of sensor 60 secured by the adapting ring 50 to plate 35. The adapting ring, shown in FIG. 4, comprises outer wall 51, top edge 58, side openings 54a and 54b, and bottom edge 56. In certain embodiments, the sensor is composed of materials unsuitable for direct attachment to the plate 35. In such cases, the adapting ring may be used to secure sensor 60 to the plate 35 without directly welding the sensor to the plate. Sensor 60 and adapting ring 50 may be attached to the luminal surface of the plate, the side that faces the interior lumen of the anchor. In other embodiments, the sensor 60 and adapting ring 50 may be attached to the abluminal surface of the plate 35, i.e., the side of the anchor facing the vessel wall. Although the cross section of adapting ring 50 is circular in FIG. 4, other shapes such as, for example, ovals or elliposoids are also encompassed by this invention.

As shown in FIG. 4, sensor 60 fits within the adapting ring 50 and the adapting ring secures the sensor onto the plate 35. In the embodiment of FIG. 4, side openings 54a and 54b allow lower housing sections 504 and 506 of the sensor to protrude, thereby securing the sensor to the bridge. The vibrating member 510 is exposed within the interior of the adapting ring. In other embodiments, not illustrated, the sensor may be fully enclosed by the adapting ring, and no portions of the sensor protrude therefrom. The adapting ring may be attached onto the plate by well-known means, including, for example, mechanical means such as tabs or clips at the bottom edge 56 that secure the adapting ring to the plate, or other means such as, for example, adhesives, welding or brazing/soldering methods as is well known in the art. Adapting ring 50 may be made of the same biocompatible material as the bridge or materials, such as, polyurethanes, polymers, or polycarbonates. Non-limiting examples of these materials are PEEK-Optima® or ChronoFlex®.

As shown in FIG. 4, adapting ring top edge 58 is fully or partially open, exposing the vibrating member 510 to the external environment after implantation. The shape of the adapting ring may be modified to account for sensors having other shapes, or where other surfaces of the enclosed sensor 60 must be exposed for proper function. In the configuration of FIG. 4, top edge 58 of adapting ring 50 may be configured to be higher than the height of sensor 60 so that it protects the vibrating member 510 from the direct on-flow of external materials both before and after implantation. The top surface of the vibrating member 510 is recessed within the adapting ring top edge 58 so that the adapting ring protects the sensor from improper contact. Additionally, an angiographic marker may be attached to the plate to indicate the location and orientation of sensor 60 for precise implantation. In one embodiment, the angiographic marker is inserted between the bottom of the sensor housing 501 and plate 35. Angiographic markers are well known in the art, and may be composed of gold, boron, tantalum, platinum iridium or similar materials. The thickness of the angiographic marker may be between 10-50 μm. In one embodiment it is 25 μm. In FIG. 4, a portion of the bridge 30 is shown with welding points 80.

FIG. 6 illustrates anchor 610 and bridge 630, where anchor 610 is in the expanded configuration and bridge 630 adopts a bowed position. Bridge 630 comprises ends 631a and 631b, attached to the anchor at rings 627a and 627b, respectively. As shown, rings 627a and 627b have different sizes. Rings may vary in size depending on the amount of material desired and the amount of strain on the expandable anchor. Plate 635 is located at the center of bridge 630. The width of bridge 630 of FIG. 6 is substantially smaller than the width of the bridge 30 of FIG. 1. The width of the bridge may be varied depending on the amount of material desired on the device. The width of plate 635 is larger than the width of bridge 630. Sensor 60 is in direct contact with plate 635, and is secured by adapting ring 50. Adapting ring 50 may be welded or otherwise adhered to plate 635 at areas 660. FIG. 6 illustrates the abluminal side of plate 635, and the sensor is attached to the luminal side of plate 635. The anchor 610 may comprise angiographic marker site 650 for insertion of an angiographic marker, which may be optionally located at any location on anchor 610. In this embodiment, marker site 650 is further attached to ring 627a.

Another aspect of the invention relates to methods of manufacturing the implantable device. Generally, the implantable device may be manufactured by separately forming the bridge and the anchor from a flat sheet or planar sheet of biocompatible material or from a tube, then joining the two pieces together. Alternatively, the bridge and anchor may be formed as a single unit.

On the method of manufacturing the device as a single unit, the method comprises (a) manufacturing of the bridge and anchor as a single unit, (b) heat treating the bridge and anchor to a thermomechanically preset shape, and (c) assembly of the adapting ring and sensor to the bridge. The method may further comprise crimping and securing the device on a delivery catheter. Optionally, an angiographic marker can be attached to the sensor.

The manufacture of the bridge and anchor as a single unit may be achieved by laser or chemical etching from a tube or a flat sheet or planar sheet, wherein the flat or planar pattern is rolled and welded into a tube.

The heat treatment step comprises securing the anchor onto a mandrel, wherein the bridge is positioned over a preshaped divot and applying heat and force necessary to impart a thermomechanically preset shape to the expanded anchor configuration and bow into the bridge. Depending on the desired expanded size of the anchor, e.g., diameters of 10, 8 or 6 mm, appropriately sized mandrels are used. Preferably, the anchor is tightly secured onto the mandrel so that heat can be evenly applied to the anchor. Where the anchor and bridge is formed as a single unit, the mandrel further comprises a divot that aligns with the bridge, so that the bridge is bowed within the divot during the heat treatment.

Figure 7A:
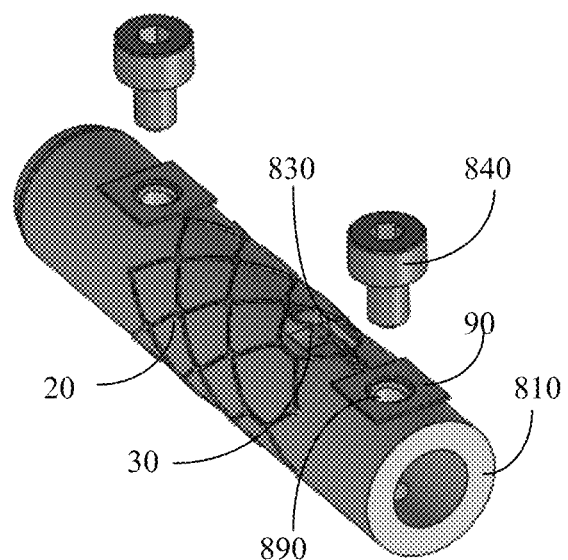
FIGS. 7A-7D illustrates the heat treatment process in accordance with the invention.

FIGS. 7A-D demonstrate one embodiment of the securement of the anchor and bridge for the heat treatment process. In FIG. 7A, anchor 20 and bridge 30, formed as a single unit, is placed on mandrel 810. Mandrel 810 comprises a divot 830, which is an indentation on the surface of the mandrel, upon which bridge 30 is aligned. During the manufacturing process of the anchor 20, the anchor may comprise one or more orienting panels 90, which, when placed on the mandrel, aligns the anchor with one or more orienting holes 890 on the mandrel. Each panel 90 is secured to the mandrel with an orienting screw 840, which fits into orienting hole 890 on the mandrel. The alignment of the orienting panel 90, orienting hole 890 and orienting screw 840 ensures alignment of bridge 30 with divot 830. Orienting panel 90 may be any shape or size, and is not limited to the embodiment depicted in FIGS. 7A-7D.

Figure 7B:
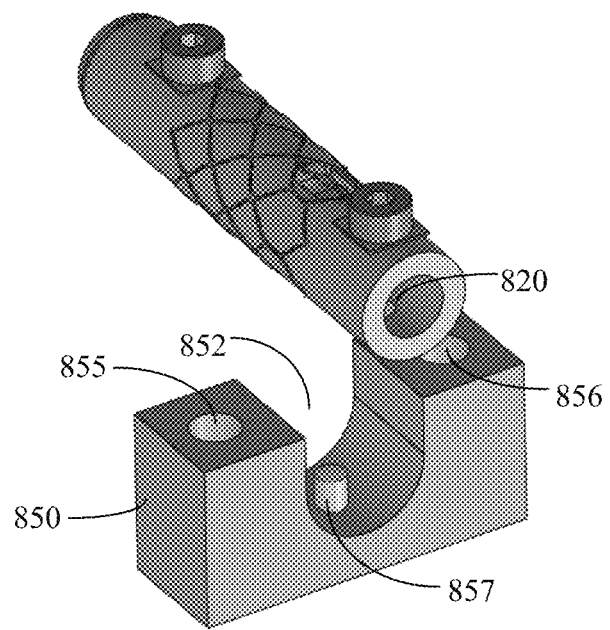
Figure 7C:
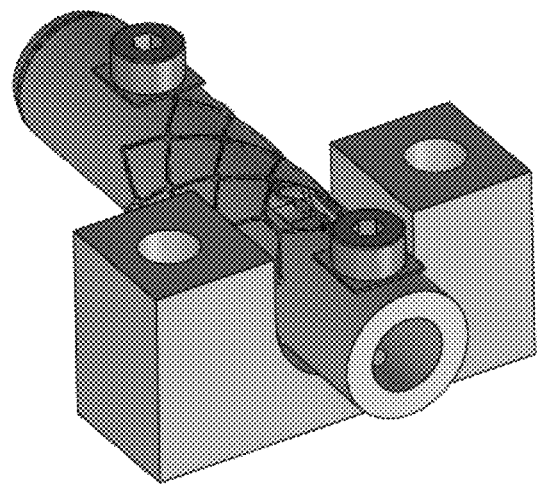

Once the anchor 20 is secured onto the mandrel 810, the mandrel is placed into socket 852 of lower block 850, shown in FIGS. 7B and 7C. Socket 852 is configured to secure mandrel 810. Lower block 850 further comprises two block holes 855 and 856 and stud 857. In FIG. 7C, stud 857 fits into a corresponding hole or depression 820 on mandrel 810, thereby preventing any lateral shifting of the mandrel with respect to the lower block 850. The orientation of stud 857 and depression 820 also ensures that divot 830 is between the two block holes 855.

Figure 7D:
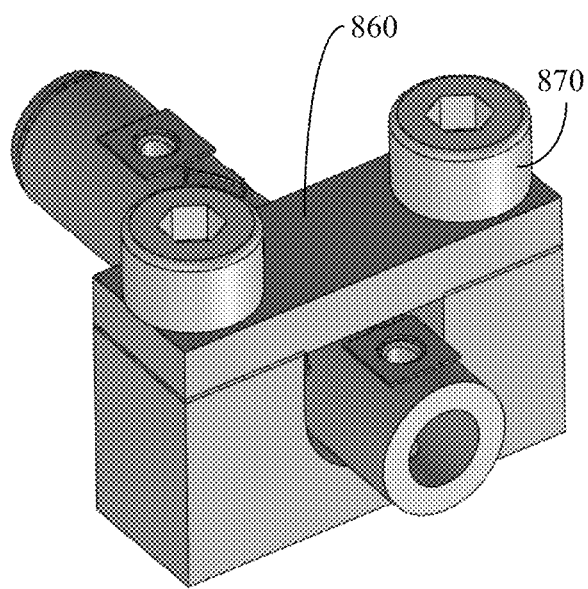

FIG. 7D illustrates the fully assembled heat treatment block containing the anchor and bridge. In FIG. 7D, upper block 860 is positioned on top of lower block 850, and secured to lower block 850 by block screws 870. Upper block 860 contains a protrusion (not shown) matching the shape of divot 830 on the mandrel. Upper block 860 is secured onto lower block 850 pushing the protrusion into divot 830, forcing the bridge 30 downward into the mandrel divot, producing the bowed shape to bridge 30. This step is accompanied by heat treating to a thermomechanically preset shape. Optionally, orienting screws 840 may be removed after the upper block 860 is secured to lower block 850. Removal of the orienting screws 840 prior to the heat treatment may advantageously provide more efficient heat treatment. Orienting panel(s) 90 may be removed from the anchor at any time following the removal of the orienting screws 840.

During the heat treatment, the device may be heated as is known in the art for forming shape-memory configurations. In one embodiment, the anchor may be heated to 600±3° C. for approximately 25-40 minutes. Alternatively, the anchor may be heated to 320±3° C. for approximately 70 to 85 minutes. Suitable heat treatment systems for this method are known in the art. Heat treatment to a thermomechanically preset shape forms the relaxed state of the anchor and bridge, i.e., the expanded anchor and bowed bridge.

After heat treatment is completed, the sensor and adapting ring are assembled onto the bridge. The heat-treated anchor is placed over a jig having an indentation within which the adapting ring, sensor and/or angiographic marker is placed. When the bridge is properly aligned with the indentation on the jig, the adapting ring is secured to the plate by methods known in the art, e.g., welding. Thereafter, the anchor, with the adapting ring, sensor, and/or marker may be removed from the jig for assembly onto a delivery device.

Figure 8:
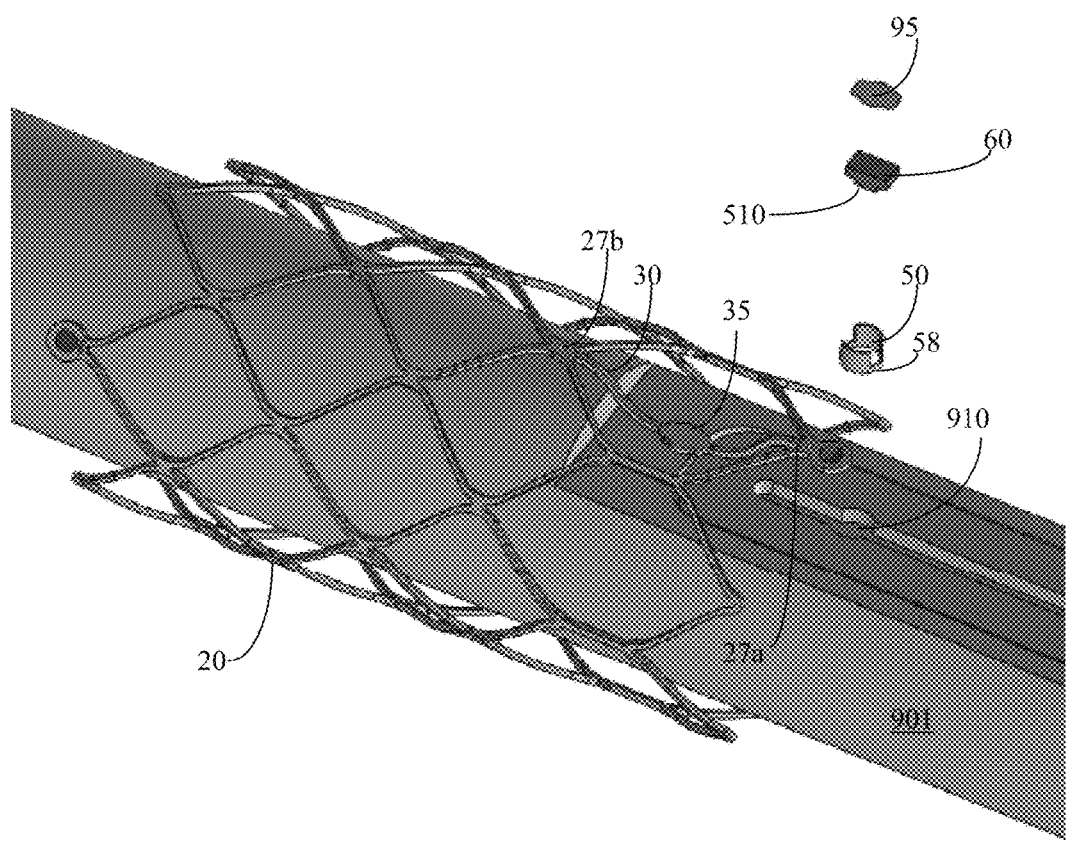
FIG. 8 illustrates the jig used to attach the adapting ring and sensor to the anchor and bridge following heat treatment.

FIG. 8 illustrates one embodiment of the process for attaching the adapting ring and sensor onto the bridge. The heat treated anchor 20 with bridge 30 is placed onto cylindrical jig 901 having indentation area 910. The adapting ring is placed into indented area 910, with the top edge 58 facing toward the center of the jig. The sensor 60 is then placed, with the vibrating member 510 face down, into the adapting ring 50. An optional angiographic marker 95 may also be placed within the jig. The placement of the adapting ring, sensor and optional angiographic marker into indented area 910 may be performed prior to or after anchor 20 is placed on the jig. Anchor 20 is positioned so that plate 35 aligns with the adapting ring 50 in indented area 910. Thereafter, the adapting ring 50 may be secured onto the plate 35, by known means, e.g., welding the adapting ring to the plate, completing the assembly of the device.

The assembled device may be crimped by any conventional means known in the art, and secured onto a delivery device. One such delivery device may be a delivery catheter. Existing crimping devices and methods for securing the crimped anchor are well known in the art, for example, as described in U.S. Pat. Nos. 6,387,118, 6,108,886, 6,092,273, 6,082,990, 6,074,381, 6,063,102, 5,992,000, and 7,225,518, the contents of which are herein incorporated by reference.

In another embodiment of the invention, the device can be manufactured from separate anchor and bridge components. This method relates to making an implantable device comprising an expandable anchor, a bridge and a sensor, whereby the expandable anchor has a compressed and expanded configuration, said bridge is aligned with the members of the anchor when said anchor is in the compressed configuration, and said bridge protrudes into said lumen when said anchor is in the expanded configuration, comprising the steps of: (a) manufacturing the anchor; (b) manufacturing the bridge; (c) attaching the bridge to the anchor; (d) heat treating the anchor and the bridge to a thermomechanically preset shape; and (e) assembling the sensor to the bridge. The method may further comprise crimping and securing the device on a delivery catheter. Optionally, an angiographic marker can be attached to the sensor. Step (d) may be performed prior to step (c). Also, step (e) may be performed prior to step (d).

The manufacture of the anchor may be achieved by laser or chemical etching from a tube or a flat sheet or planar sheet, then rolled into a tube, which are known stent manufacturing procedures in the art. The bridge may be similarly manufactured by laser or chemical etching from biocompatible material.

Forming the anchor and the bridge separately allows the bridge to be exposed to a different heat treatment than the anchor, and thus may have different thermomechcanical properties than that of the anchor. The heat treatment step may be performed by placing and securing the anchor on a mandrel, then applying heat necessary to impart a shape memory to the anchor. The anchor may be secured onto the mandrel by known methods in the art. The size of the mandrel may be chosen depending on the desired size of the anchors, e.g., 10, 8 or 6 mm. Preferably, the anchor is tightly secured onto the mandrel so that heat can be evenly applied to the anchor.

During heat treatment, the anchor may be heated as is known in the art for forming shape-memory configurations. In one embodiment, the anchor may be heated to 600±3° C. for approximately 25-40 minutes. Alternatively, the anchor may be heated to 320±3° C. for approximately 70 to 85 minutes. Suitable heat treatment systems for this method are well known in the art. Heat treatment to a thermomechanically preset shape forms the relaxed state of the anchor and bridge, i.e., the expanded anchor and bowed bridge.

After heat treatment is completed, the anchor, bridge, sensor and adapting ring are assembled. The jig 901 of FIG. 8 may also be used in the assembly of the anchor, bridge, sensor and adapting ring. First, the adapting ring is placed into indented area 910, with the top edge 58 facing down into the jig. The sensor is then placed, with the vibrating member 510 faced down into the adapting ring 50. An optional angiographic marker 95 may be placed within the jig. Lastly, the bridge is placed into indented area 910, aligning the plate with the adapting ring.

Alternatively, the bridge, adapting ring, sensor and/or angiographic mark may be pre-assembled by any known means prior to placement within jig 901. In the pre-assembly, the sensor may be secured to the bridge by the adapting ring, with an optional angiographic marker placed between the sensor and the bridge. The pre-assembled bridge and sensor can be placed into indented area 910 as a single component. Thereafter, anchor 20 is aligned with the bridge 30 and the bridge 30 can be secured to the anchor, for example, by welding.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

The invention claimed is:

1. An implantable device comprising:
    an anchor having a first serpentine ring and a second serpentine ring defining a lumen along a longitudinal axis, and having a compressed configuration and an expanded configuration, and
    a bridge having a first end attached to said first serpentine ring and a second end attached to said second serpentine ring, said first end is separated from the second end at a first distance and said bridge is aligned with the longitudinal axis of the anchor when said anchor is in the compressed configuration, and said first end is separated from the second end at a second distance when said anchor is in the expanded configuration, and said bridge protrudes into said lumen when said anchor is in the expanded configuration, said second distance is less than said first distance.

2. The implantable device of claim 1, wherein said first serpentine ring and said second serpentine ring define a plurality of cells.

3. The implantable device of claim 2, wherein the said first serpentine ring and said second ring are connected between a peak of said first serpentine ring and a valley of said second serpentine ring.

4. The implantable device of claim 3, wherein said first end of the bridge is attached to the peak of the first serpentine ring, and said second end of the bridge is attached to the valley of the second serpentine ring.

5. The implantable device of claim 4, wherein a distance between said peak of said first serpentine ring and said valley of said second serpentine ring is greater in the compressed configuration than in the expanded configuration.

6. The implantable device of claim 2, wherein a cell of the plurality of cells has two vertices on opposite ends of said cell, and said ends of the bridge are attached to said vertices.

7. The implantable device of claim 6, wherein a distance between said vertices is greater in the compressed configuration than in the expanded configuration.

8. The implantable device of claim 1, wherein said first serpentine ring and said second serpentine ring each comprises a plurality of peaks and valleys.

9. The implantable device of claim 1, wherein the bridge is attached to the anchor by welding, soldering, brazing, or through adhesives.

10. The implantable device of claim 1, wherein the bridge and the anchor are formed as a single unit.

11. The implantable device of claim 1, wherein the bridge comprises a plate.

12. The implantable device of claim 11, wherein a sensor is embedded within said plate.

13. The implantable device of claim 11, wherein a sensor is attached to said plate.

14. The implantable device of claim 13, wherein the sensor is configured to measure fluid pressure.

15. The implantable device of claim 13, wherein the sensor is coated with polyethylene glycol.

16. The implantable device of claim 13, wherein said sensor is an encapsulated sensor.

17. The implantable device of claim 13, further comprising an adapting ring configured for attaching said sensor to said plate.

18. The implantable device of claim 17, wherein the bottom end of the adapting ring is secured to the plate by a locking tab, welding, soldering, brazing, or adhesives.

19. The implantable device of claim 17, wherein the sensor is recessed within the adapting ring.

20. The implantable device of claim 17, wherein the adapting ring comprises an opening configured for a protrusion of the sensor.

21. The implantable device of claim 1, wherein the bridge is substantially straight.

22. The implantable device of claim 1, wherein the bridge contains a plurality of loops.

23. The implantable device of claim 1, further comprising an angiographic marker attached to the bridge.

24. The implantable device of claim 1, wherein said anchor can return to the compressed configuration after partial expansion.

25. The implantable device of claim 1, wherein the anchor is self-expandable.

26. An implantable device comprising: an anchor having a first serpentine ring having a plurality of peaks and valleys and a second serpentine ring having a plurality of peaks and valleys, wherein the plurality of valleys of the first serpentine ring are connected to the plurality of peaks of the second serpentine ring, said anchor having a compressed configuration and an expanded configuration; and a bridge having a first end and a second end, said first end attached to one of the plurality of peaks of the first serpentine ring and said second end attached to one of the plurality of valleys of the second serpentine ring, said one of the plurality of peaks of the first serpentine ring is separated from said one of the plurality of valleys of the second serpentine ring by a first distance in the compressed configuration, and said one of the plurality of peaks of the first serpentine ring is separated from said one of the plurality of valleys of the second serpentine ring by a second distance in the expanded configuration, said second distance is less than said first distance, wherein said bridge is in a flat position when said anchor is in the compressed configuration, and said bridge is in a bowed position and protrudes into a lumen of the anchor when said anchor is in the expanded configuration.

* * * * *